(12) United States Patent
Jolivet-Reynaud et al.

(10) Patent No.: US 6,555,091 B1
(45) Date of Patent: Apr. 29, 2003

(54) POLYPEPTIDE CAPABLE OF REACTING WITH ANTIBODIES OF PATIENTS SUFFERING FROM MULTIPLE SCLEROSIS AND USES

(75) Inventors: Colette Jolivet-Reynaud, Bron (FR); Hervé Perron, Lyons (FR); Bernard Mandrand, Villeurbanne (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/403,343

(22) PCT Filed: Apr. 29, 1998

(86) PCT No.: PCT/FR98/00870

§ 371 (c)(1),
(2), (4) Date: Oct. 18, 1999

(87) PCT Pub. No.: WO98/49285

PCT Pub. Date: Nov. 5, 1998

(30) Foreign Application Priority Data

Apr. 29, 1997 (FR) .............................. 97 05679
Dec. 31, 1997 (FR) .............................. 97 16870

(51) Int. Cl.$^7$ ................ A61B 5/055; G01N 33/53; C12N 1/00; C07K 7/00; A61K 38/00
(52) U.S. Cl. ................ 424/9.34; 435/7.1; 435/810; 435/975; 530/326; 530/300; 514/2
(58) Field of Search ................ 530/326, 300; 514/2; 435/7.1, 810, 975; 424/9.35

(56) References Cited

U.S. PATENT DOCUMENTS

| 5,420,244 A | 5/1995 | Rudolph et al. |
| 5,639,641 A | * 6/1997 | Pedersen et al. ............ 435/69.6 |

FOREIGN PATENT DOCUMENTS

| EP | 0 569 309 A1 | 6/1993 |
| EP | 2 715 938 | 4/1994 |
| FR | 2 686 521 | 3/1992 |
| FR | 2 689 519 | 3/1992 |
| FR | 2 689 520 | 3/1992 |
| FR | 2 686 788 | 5/1992 |
| FR | 2 715 937 | 4/1994 |
| FR | 2 715 939 | 4/1994 |
| FR | 2 737 500 | 3/1995 |
| WO | WO 94/26886 | 11/1994 |
| WO | WO 96/33275 | 10/1996 |
| WO | WO 97/06260 | 2/1997 |

OTHER PUBLICATIONS

Shen et al., GenBank Accession No. T20376, Oct. 17, 1996.*

J. Sambrook, E.F. Fritsch and T. Maniatis, "Molecular Cloning", *A Laboratory Manual Second Edition*, 1989.

H. Perron, C. Geny, A. Laurent, C. Mouriquand, J. Pellat, Perret and J.M. Seigneurin, "Leptomeningeal Cell Line From Multiple Sclerosis With Reverse Transcriptase Activity And Viral Particles", *Institut Pasteur/Elsevier Paris*, 1989, 140m 5454–561.

Jamie K. Scott and George P. Smith "Searching for Peptide Ligands with an Epitope Library", Science, vol. 249, 1990, 386–90.

Pir 1 Accession No.E35324, Kigone Et Al.,1991.

Pir 2 Accession No. C60474, Fleishmann Et Al., 1995.

GeneSeq Accession No. U05510, Spaote Et Al., 1997.

GenBank Accession No. M37730, Yang Et Al., 1979.

Swiss–Prot Accession No. P01391, Arnberg Et Al., 1986.

Swiss–Prot Accession No. P07033, Camici Et Al., 1988.

Pir Accession No. A42804, Ohashi Et Al., 1992.

Swiss–Prot Accession No. P502821, Chan Et Al., 1998.

Dybwad, Anne et al., "Probing for Cerebrospinal Fluid Antibody Specificities by a Panel of Random Peptide Libraries," Autoimmunity, vol. 25, 1997, pp. 85–59.

Cortese, I et al., "Identification of peptides binding to IgG in the CSF of Multiple Sclerosis Patients," Multiple Sclerosis, vol. 4,1998, pp. 31–36.

Sioux, Mouldy, "Selection of Ligands for Polyclonal Antibodies from Random Peptide Libraries: Potential Identification of (Auto)Antigens that may Trigger B and T Cell Responses in Autoimmune Diseases," Clinical Immunology and Immunopathology, vol. 79, No. 2, May 1996, pp. 105–114.

Cortese, Irene et al., "Identification of Peptides Specific for Cerebrospinal Fluid Antibodies in Multiple Sclerosis by Using Phage Libraries,," Proc. Nat. Acad. Sci. USA, vol. 93, 1996, pp. 11063–11067.

Mansuelle, Pascal et al., "Amino Acid Sequence of Toxin IV from the Androctonus australis Scorpion: Differing Effects of Natural Mutation In Scorpion α–Toxins on their Antigenic and Toxic Properties," Natural Toxins, vol. 1 1998, pp. 61–69.

* cited by examiner

*Primary Examiner*—Yvonne Eyler
*Assistant Examiner*—Janet L. Andres
(74) *Attorney, Agent, or Firm*—Oliff & Berridge

(57) ABSTRACT

The invention concerns a polypeptide specifically reacting with the antibodies of patients suffering from multiple sclerosis (SEP) and whereof the peptide sequence comprises at least one sequence selected among SEQ ID No. 1 to SEQ ID NO: 19, and their equivalent sequences, and the use of this polypeptide in a reagent and a kit for detecting multiple sclerosis, an immunoreactive composition and in a method for fixing, in a biological sample, antibodies characteristic and/or specific of multiple sclerosis.

17 Claims, 6 Drawing Sheets

FIG 3

```
          10         20         30         40         50
 1234567890 1234567890 1234567890 1234567890 1234567890
 CTCCTTCCCC AACTAATAAG GACCCCCCTT TCAACCCAAA CAGTCCAAAA      50
  L  L  P  Q  L  I  R  T  P  L  S  T  Q  T  V  Q  K

GGACATAGAC AAAGGAGTAA ACAATGAACC AAAGAGTGCC AATATTCCCT     100
  D  I  D  K  G  V  N  N  E  P  K  S  A  N  I  P  W

GGTTATGCAC CCTCCAAGCG GTGGGAGAAG AATTCGCCC  AGCCAGAGTG     150
  L  C  T  L  Q  A  V  G  E  E  F  G  P  A  R  V

CATGTACCTT TTTCTCTCTC ACACTTGAAG CAAATTAAAA TAGACCTAGG     200
  H  V  P  F  S  L  S  H  L  K  Q  I  K  I  D  L  G

TAAATTCTCA GATAGCCCTG ATGGCTATAT TGATGTTTTA CAAGGATTAG     250
  K  F  S  D  S  P  D  G  Y  I  D  V  L  Q  G  L  G

GACAATCCTT TGATCTGACA TGGAGAGATA TAATATTACT GCTAAATCAG     300
  Q  S  F  D  L  T  W  R  D  I  I  L  L  N  Q

ACGCTAACCT CAAATGAGAG AAGTGCTGCC ATAACTGGAG CCCGAGAGTT     350
  T  L  T  S  N  E  R  S  A  A  I  T  G  A  R  E  F

TGGCAATCTC TGGTATCTCA GTCAGGTCAA TGATAGGATG ACAACGGAGG     400
  G  N  L  W  Y  L  S  Q  V  N  D  R  M  T  T  E  E

AAAGAGAACG ATTCCCCACA GGGCAGCAGG CAGTTCCCAG TGTAGCTCCT     450
  R  E  R  F  P  T  G  Q  Q  A  V  P  S  V  A  P
                              ‾‾‾‾‾‾‾
 CATTGGGACA CAGAATCAGA ACATGGAGAT TGGTGCCGCA GACATTTA       498
  H  W  D  T  E  S  E  H  G  D  W  C  R  R  H  L
```

FIG 4

```
              10         20         30         40         50
     1234567890 1234567890 1234567890 1234567890 1234567890
     CACAGGGAA AGGAAGAAAA TCCTACTGCC TTTCTGGAGA GACTAAGGGA    50
      H R G K   E E N   P T A   F L E R   L R E

GGCATTGAGG AAGCATACCA GGCAAGTGGA CATTGGAGGC TCTGGAAAAG   100
      A L R   K H T R   Q V D   I G G   S G K G

GGAAAAGTTG GAAAAGTAT ATGTCTAATA GGGCTTGCTT CCAGTGTGGT   150
      K S W   E K Y   M S N R   A C F   Q C G

CTACAAGGAC ACTTTAAAAA AGATTGTCCA ATAGAAATAA GCCACCACCT   200
      L Q G H   F K K   D C P   I E I S   H H L

CGTCCATGCC CCTTATGTCA AGGGAATCAC TGGAAGGCCC ACTGCCCCAG   250
      V H A   P Y V K   G I T   G R P   T A P G

GGGATGAAGG TCCTCTGAGT CAGAAGCCAC TAACCA                 286
      D E G   P L S   Q K P L T
```

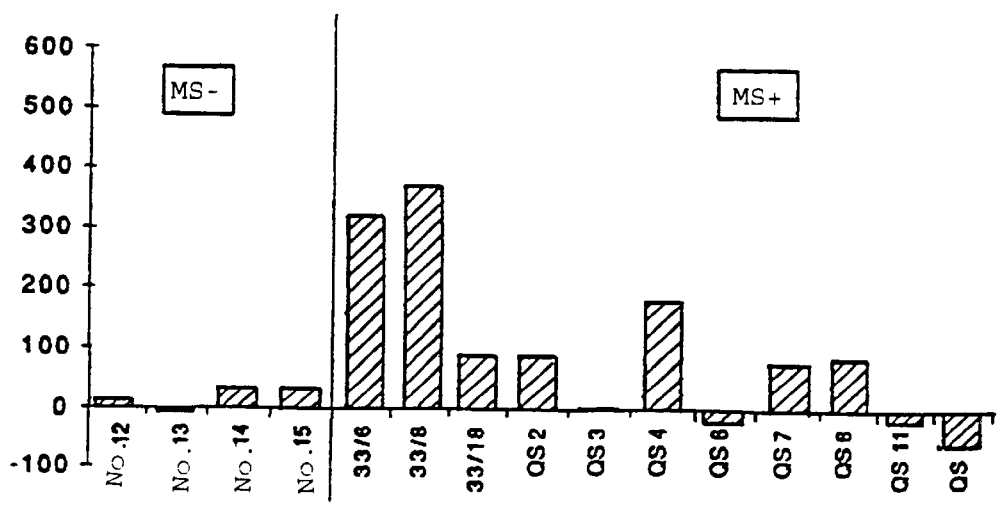

FIG 5

FIG. 7A
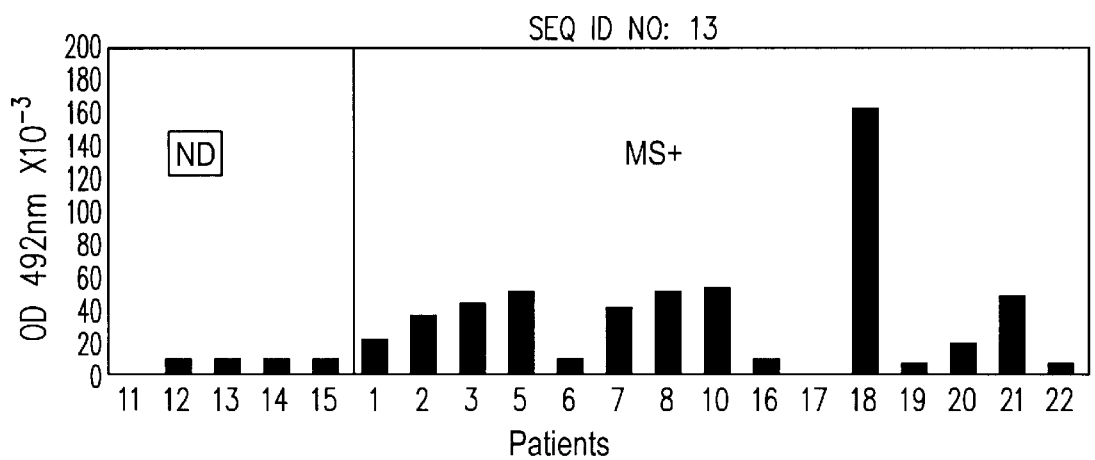
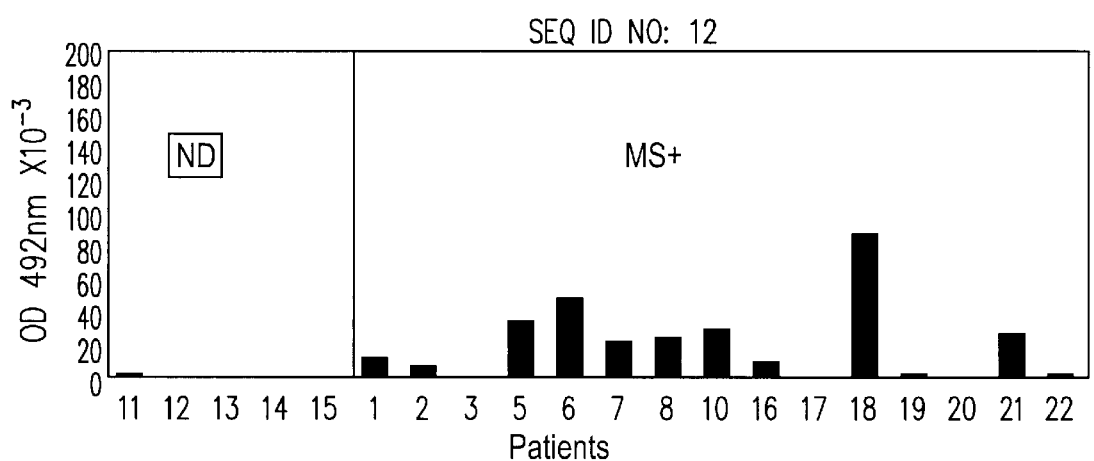
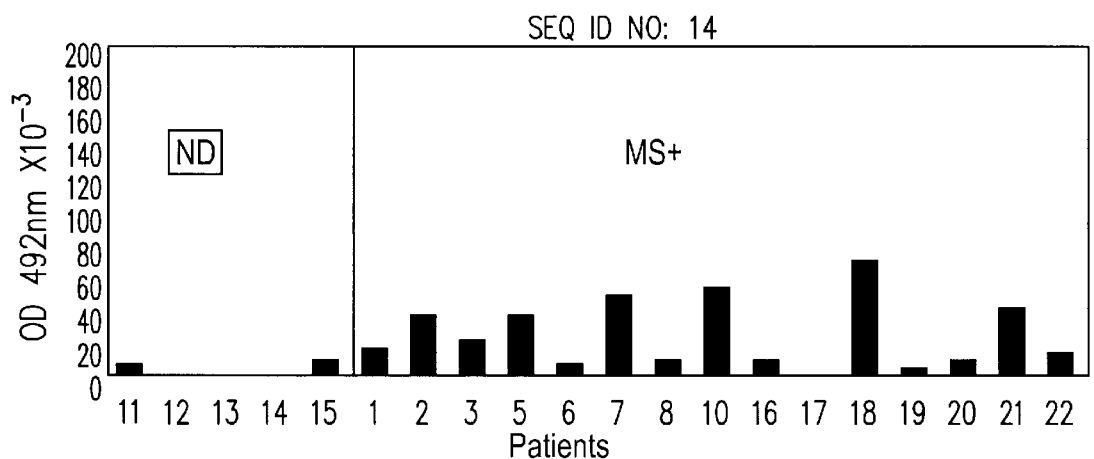

FIG. 7B
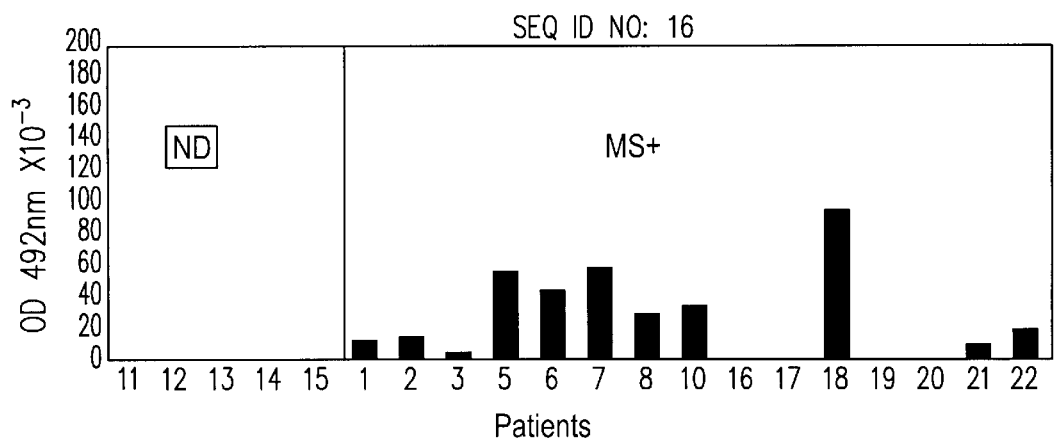
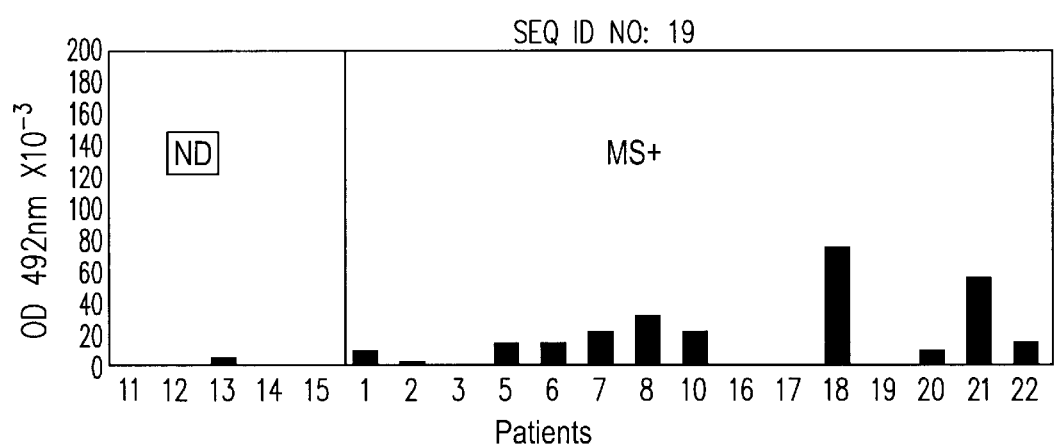
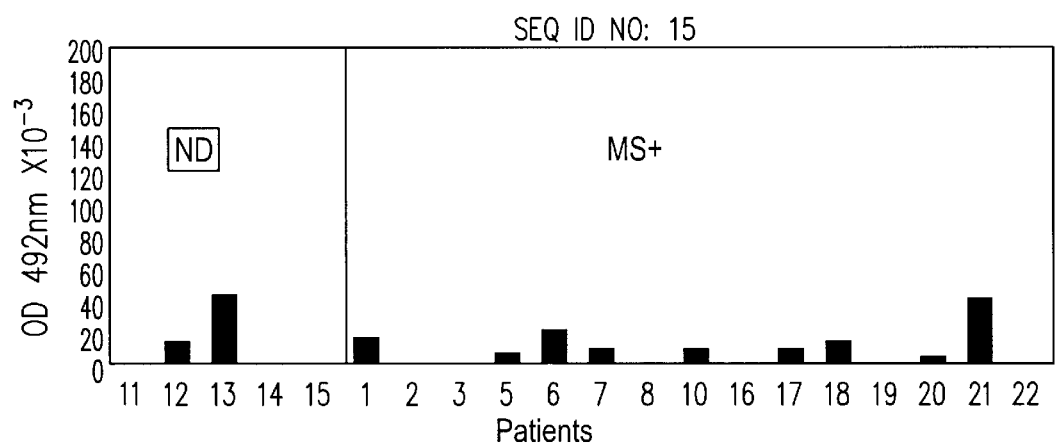

POLYPEPTIDE CAPABLE OF REACTING WITH ANTIBODIES OF PATIENTS SUFFERING FROM MULTIPLE SCLEROSIS AND USES

The present invention relates to the determination of immunoreactive polypeptides capable of reacting specifically with the antibodies of patients suffering from multiple sclerosis (MS), and the use of these polypeptides.

The Applicant has defined a polypeptide capable of reacting specifically with the antibodies of patients suffering from multiple sclerosis, and which must additionally meet at least any one of the following definitions, provided that said polypeptide is different from the polypeptides having one of the following sequences: SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27:

- its peptide sequence comprises at least one sequence chosen from SEQ ID NO: 1 to SEQ ID NO: 19, and their equivalent sequences;
- its peptide sequence consists of a sequence chosen from SEQ ID NO: 1 to SEQ ID NO: 19, and their equivalent sequences; preferably, it is chosen from SEQ ID NO: 1, SEQ ID NO: 2, SEQ ID NO: 3, SEQ ID NO: 4, SEQ ID NO: 10, SEQ ID NO: 11, SEQ ID NO: 12, SEQ ID NO: 13, SEQ ID NO: 14, SEQ ID NO: 16 and SEQ ID NO: 19;
- it comprises a sequence equivalent to SEQ ID NO: 11, said equivalent sequence exhibiting, for a succession of 8 contiguous amino acids, at least 35% (which corresponds to at least 3 amino acids), preferably 50% (which corresponds to at least 4 amino acids) identity, and/or at least 60% (which corresponds to about at least 5 amino acids), preferably 75% (which corresponds to at least 6 amino acids) homology with a sequence of the foot-and-mouth disease virus SAT3 protein, said polypeptide being different from the whole or part of said SAT3 protein;
- it comprises a sequence equivalent to SEQ ID NO: 13 exhibiting, for a succession of 12 contiguous amino acids, at least 40%, preferably 50% identity, and/or at least 55%, preferably 65% homology with a sequence p30/p10/5'v-fsm of the coding region of the feline sarcoma virus (FSV) [NCBI reference gi/554646], said polypeptide being different from the whole or part of said sequence p30/p10/5'v-fsm.

Moreover, the work by the Applicant, in the search for an etiology of MS, has led to the discovery of the existence of at least one pathological and/or infective agent, the retrovirus MSRV-1, in particular associated with multiple sclerosis.

The techniques for the culture and detection of retroviral material which were used in the work carried out by the Applicant on a multiple sclerosis (MS) associated agent are described in French Patent Applications 92 04322, 92 13447, 92 13443, 92 01529, 94 01530, 94 01531, 94 01532 and in the publication by H. PERRON et al. (Res. Virol. 1989; 140, 551–561) (the content of which is incorporated by reference into the present description).

This retrovirus may be derived from a viral strain chosen from the strains called, respectively, POL-2, deposited on 22.07.1992 at the ECACC under the accession number V92072202, and MS7PG deposited on 08.01.93 at the ECACC under the accession number V93010816, or produced by a cell line chosen from the lines called, respectively, PLI-2 deposited on 22.07.1992 at the ECACC under the accession number 92072201, and LM7PC deposited on 08.01.93 at the ECACC under the accession number 93010817.

Among the polypeptides of the invention, the Applicant has determined a polypeptide (generically called pxMSRV-1 in the remainder of the description) capable of reacting specifically with at least one biological fluid from a patient in whom the MSRV-1 viral sequences have been detected. According to the invention, this polypeptide possesses a peptide sequence which comprises at least one sequence chosen from SEQ ID NO: 1, SEQ ID NO: 2, SEQ ID NO: 3, SEQ ID NO: 4, and their equivalent sequences, said polypeptide being different from the polypeptides having any one of the following sequences: SEQ ID NO: 20, SEQ ID NO: 21, SEQ ID NO: 25. Preferably, the sequence of the polypeptide pxMSRV-1 consists of SEQ ID NO: 1, SEQ ID NO: 2, SEQ ID NO: 3 or SEQ ID NO: 4.

Before disclosing the invention in greater detail, various terms used in the description and the claims are defined below.

"Polypeptide" designates a peptide, in the isolated state, exhibiting a succession of a variable number of amino acids, such as an oligopeptide, a protein, a fusion protein, a fusion peptide, a synthetic peptide. A polypeptide may be obtained by various techniques well known to persons skilled in the art, and in particular by chemical synthesis or by genetic recombination techniques. The polypeptides according to the invention may be obtained by methods of conventional synthesis, for example with an automated peptide synthesizer, or by genetic engineering techniques comprising the insertion of a DNA sequence encoding said polypeptide into an expression vector such as a plasmid or a virus, and the transformation of cells with this expression vector and culture of these cells.

A polypeptide of the invention advantageously contains at most 50 amino acids, preferably at most 30 amino acids, or better still at most 20 amino acids, or even at most 15 amino acids.

"Peptide sequence equivalent to a reference peptide sequence is understood to mean an amino acid sequence modified by insertion and/or deletion and/or substitution and/or extension and/or shortening and/or chemical modification of one or more amino acids, as long as these modifications substantially preserve or even develop the immunoreactive properties of said reference peptide sequence. Advantageously, said equivalent sequence exhibits, for at least a succession of 6 amino acids, a percentage identity of at least 40%, preferably of at least 50%, or better still of at least 60% or even 70%, with said reference sequence. This percentage identity is calculated according to the following steps: a succession of 6 contiguous amino acids of the sequence analyzed is compared with a succession of 6 contiguous amino acids of the reference sequence, the amino acids which are common between the analyzed sequence and the reference sequence, located at the same position, are determined and the percentage identity is deduced.

"Equivalent sequence" is thus understood to mean in particular the sequences in which one or more amino acids are substituted by one or more other amino acids; the sequences in which one or more amino acids of the L series are replaced by an amino acid of the D series, and vice versa; the sequences in which a modification of the side chains of the amino acids, such as an acetylation of the amine functions, a carboxylation of the thiol functions, an esterification of the carboxyl functions, is introduced; a modification of the peptide bonds such as, for example, the carba, retro, inverse, retro-inverse, reduced and methyleneoxy bonds.

The equivalence of a peptide sequence relative to a reference peptide sequence may be defined by its identity or its homology, expressed as a percentage, with said reference sequence. This percentage is determined, for a succession of a given number of contiguous amino acids, by aligning the two sequences, moving one relative to the other, and comparing the amino acids in the two sequences. The percentage identity is determined from the number of amino acids which are identical to the amino acids of the reference sequence, at the same position. The percentage homology is determined from the number of amino acids which are equivalent to amino acids of the reference sequence, at the same position. Using the BLAST program (BLAST p matrix Blosum62) publicly available (on the Internet, at the National Center for Biotechnology Information (NCBI), Bethesda, USA), persons skilled in the art are in a position to know if the sequence which they have selected exhibits the percentage homology required according to the invention, compared with the reference sequence. In accordance with the BLAST program, two amino acids are equivalent if they possess similar physicochemical properties, such as hydrophilicity, isoelectric point.

Viral sequence of the MSRV-1 virus is understood to mean in particular all the nucleotide sequences described in French Patent Applications 92 04322, 92 13447, 92 13443, 92 01529, 94 01530, 94 01531, 94 01532, 95 09643, in the name of the Applicant.

Binding of antibodies is understood to mean the separation, isolation, detection and/or quantification of these antibodies, the enrichment of an antibody fraction, according to a specific or aspecific binding method, qualitatively and/or quantitatively.

"Polynucleotide" is understood to mean either a DNA sequence or an RNA sequence or a cDNA sequence resulting from the reverse transcription of an RNA sequence, of natural or synthetic origin, with or without modified bases.

The invention additionally relates to:
  a reagent for the detection of multiple sclerosis in a patient and/or the monitoring of a patient suffering from multiple sclerosis, comprising at least one, or consisting of a, polypeptide capable of reacting specifically with the antibodies of patients suffering from multiple sclerosis (MS) and whose peptide sequence comprises at least one sequence chosen from SEQ ID NO: 1 to SEQ ID NO: 19, and their equivalent sequences, said polypeptide being optionally labeled; as well as a kit comprising this reagent, the latter being supported on a support which is immunologically compatible with said reagent;
  a reagent for the detection of an MSRV-1 virus infection comprising at least one, or consisting of a, polypeptide pxMSRV-1 capable of reacting with at least one biological fluid from a patient in whom MSRV-1 viral sequences have been detected and whose peptide sequence comprises at least one, or consists of a, sequence chosen from SEQ ID NO: 1, SEQ ID NO: 2, SEQ ID NO: 3, SEQ ID NO: 4, and their equivalent sequences, said polypeptide being optionally labeled; as well as a kit comprising this abovementioned reagent optionally supported on a support which is immunologically compatible with said reagent;

Advantageously, a reagent of the invention comprises at least two different polypeptides as defined above and in particular three polypeptides as defined above. In a particularly preferred form, a reagent comprises the three polypeptides whose peptide sequence each consists of SEQ ID NO: 12, SEQ ID NO: 13 and SEQ ID NO: 16, respectively.

a method of binding, in a biological sample, antibodies which are characteristic of and/or specific to multiple sclerosis, consisting in bringing said sample into contact with a reagent of the invention, and after having optionally detected the presence of an immune complex, in separating the latter;
  a method of binding, in a biological sample, antibodies directed against the MSRV-1 virus, comprising the steps consisting is bringing said sample into contact with a reagent of the invention comprising at least one polypeptide pxMSRV-1, and after having optionally detected the presence of an immune complex, in separating the latter;
  according to a preferred embodiment of any of the methods of binding of the invention, the sample is chosen from serum, cerebrospinal fluid and urine;
  an immunotherapeutically active composition, in particular a vaccine preparation, comprising at least one polypeptide capable of reacting specifically with the antibodies of patients suffering from multiple sclerosis (MS) and whose peptide sequence comprises at least one sequence chosen from SEQ ID NO: 1 to SEQ ID NO: 19, and their equivalent sequences, and optionally a support for said polypeptide and/or a pharmaceutically acceptable excipient;
  the use of at least one polypeptide capable of reacting specifically with the antibodies of patients suffering from multiple sclerosis (MS) and whose peptide sequence comprises at least one sequence chosen from SEQ ID NO: 1 to SEQ ID NO: 19, and their equivalent sequences, for binding, in a biological sample, antibodies which are characteristic of and/or specific to multiple sclerosis, and the use of at least one polypeptide pxMSRV-1 of the invention for binding, in a biological sample, antibodies directed against the MSRV-1 virus; and
  a polynucleotide whose nucleotide sequence comprises a sequence encoding a polypeptide of the invention.

BRIEF DESCRIPTION OF THE FIGURES

The invention disclosed above is now illustrated in the following examples 1 to 6 in support of FIGS. 1 to 7B according to which:

FIG. 3 represents the nucleotide sequence and its translation into amino acids of the clone LB19; the succession of amino acids common with SEQ ID NO: 1 and SEQ ID NO: 3 is underlined;

FIG. 4 represents the partial nucleotide sequence and its translation into amino acids of the clone GM3; the succession of amino acids common with SEQ ID NO: 2 and SEQ ID NO: 4 is underlined;

FIG. 5 represents the IgM response of the polypeptide SEQ ID NO: 8 with respect to human sera, on a histogram grouping together the results expressed in optical density values (×1000) and presented in Table 4 appended to the description; the polypeptide is tested in ELISA with respect to sera diluted 1/100; the MS− sera correspond to sera from healthy individuals; the MS+ sera correspond to sera from MS patients who nave never been treated and who are all at the remission stage.

FIGS. 7A and 7B represents the IgG response of the polypeptides whose peptide sequence consists of, respectively, SEQ ID NO: 13, SEQ ID NO: 12, SEQ ID NO: 14, SEQ ID NO: 16, SEQ ID NO: 19 and SEQ ID NO: 15, with respect to CSFs diluted 1/10; the results assembled in the appended Table 5 are expressed by the difference in the optical density values obtained for the polypeptide tested and the values obtained for the HIV polypeptide used as control; ND corresponds to patients suffering from a neurological disease other than MS, and MS* corresponds to patients suffering from MS.

EXAMPLE 1

Figure 1:
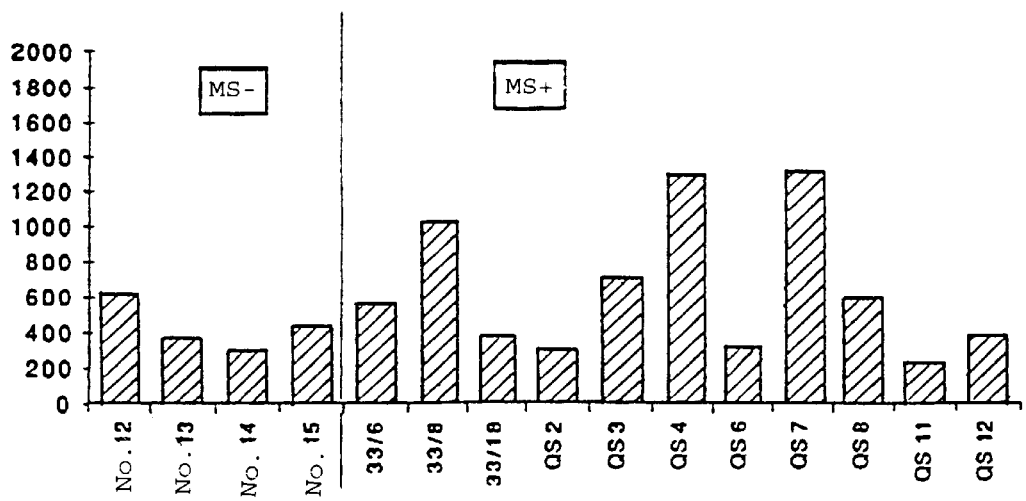
FIG. 1 represents the IgG response of the polypeptide SEQ ID NO: 3 with respect to human sera, on a histogram grouping together the results expressed in optical density values (×1000) and presented in Table 2 appended to the description; the polypeptide is tested in ELISA with respect to sera diluted 1/100; the MS– sera correspond to sera from healthy individuals; the MS+ sera correspond to sera from MS patients who have never been treated and who are all at the remission stage.

Selection of Hexapeptides Capable of Reacting Specifically with Sera from Patients Suffering from Multiple Sclerosis In a first instance, a library for expression of hexapeptides was constructed in a filmentous phage according to the method described by SCOTT and SMITH (1990, Science, 249, 386–390). This library is produced by inserting a synthetic oligonucleotide into a gene encoding a phage envelope protein (PIII protein) of which five copies are present at the surface of the phage. This oligonucleotide consists of a sequence of having a degenerate code [(NNK) 6] where NNK represents an equal mixture of the codons corresponding to the 20 amino acids and the Amber stop codon. This expression library makes it possible to obtain, at the surface of the phage, five copies of a fused protein (PIII—hexapeptide). The site of insertion of the hexapeptide into the sequence of PIII protein corresponds to the sequence: NH$_2$ Ala Asp Gly Ala [hexapep] Gly Ala Ala Gly Ala Glu Thr Val Glu COOH (SEQ ID NO: 29).

In a second instance, the bottom of a Petri dish 35 mm in diameter is treated with 1 ml of a streptavidin solution at the concentration of 10 μg/ml in 0.1M NaHCO$_3$ and incubated overnight at 4° C. After removing the streptavidin solution, a solution of 0.1M NaHCO$_3$, 0.1% of bovine serum albumin (BSA), 0.1 μg/ml of streptavidin and 0.02% of NaN$_3$ is added in order to saturate the nonspecific binding sites and the whole is incubated for 2 hours at room temperature. The Petri dish is washed 6 times with TBS buffer (0.1M Tris buffer, pH 7.2)/0.5% Tween and 10 μg of biotinylated total human antiimmunoglobulins (Southern Biotechnology Associates Inc.) are then added and incubated for 4 hours at 4° C. After an additional 1 hour of incubation in the presence of 20 μl of 2 mM biotin, the Petri dish is again washed 6 times with TBS/0.5% tween.

Moreover, 20 μl of serum (about 100 μg of total immunoglobulins) obtained from a patient suffering from multiple sclerosis at the remission stage (called patient No. 1) were preincubated for 8 hours at 4° C., with stirring, with 50 μl (about 5×10$^{12}$ virions) of a solution of wild-type phages, that is to say not containing an inserted peptide sequence. This makes it possible to eliminate any possible binding of the immunoglobulins to phage proteins other than the inserted peptide sequence. This mixture is added to the Petri dish treated as described above and incubated overnight at 4° C., with stirring. This makes it possible to obtain, in a known manner, Petri dishes at the bottom of which said antibodies are immobilized by means of streptavidin and biotinylated human total antiimmunoglobulins.

After 10 new washes in TBS/0.5% tween buffer, a sample of the expression library containing about 10$^{12}$ virions is then incubated for four hours at 4° C. in the presence of said antibodies bound to the bottom of the Petri dish. After several washes with TBS, the phages which remained bound to the antibodies contained in the serum of patient No.1 are eluted with 400 μl of a 0.1N HCl solution, pH 2.2, containing 0.1% BSA, and then neutralized with 75 μl of a 1M Tris-HCl solution, pH 9.1.

After concentrating to 100 μl, the suspension of eluted phages is subjected to an amplification step by infecting a suspension at 5×10$^9$ bacteria/ml of a strain of E. coli (K91Kan). The infected bacteria (see Sambrook et al., 1989. Molecular Cloning : A Laboratory Manual, 2nd Edition, Cold Spring Harbor Laboratory, Cold Spring Harbor) are incubated for 45 minutes at 37° C. in 20 ml of NZY medium (tryptone 10 g/l, yeast extract 5 g/l, NaCl 5 g/l, pH adjusted to 7) containing 0.2 μg/ml of tetracycline. The concentration of tetracycline in the medium is then raised to 20 mg/ml. Given that the infectious phages carry a tetracycline resistance gene, only the bacteria which have been infected by the phage are amplified. The culture of the bacteria is continued overnight at 37° C. After centrifugation of the culture in order to remove the bacterial cells, 3 ml of polyethylene glycol (PEG) 16.3%–NaCl 3.3M are added to the supernatant in order to precipitate the phages present. After overnight incubation at 4° C. and a centrifugation, the phage pellet is taken up in 1 ml of TBS (0.1M Tris buffer, pH 7.2) and reprecipitated with 150 μl of PEG/NaCl. A centrifugation makes it possible to obtain a phage pellet which is resuspended in 200 μl of TBS. The phage concentration after this amplification is about 2×10$^{13}$ virions/ml.

The 2nd selection or "biopanning 2" is carried out according to the protocol described above using 20 μl of serum from patient No.2 and about 10$^{12}$ virions derived from the Preceding amplification step.

Likewise, the 3rd selection will be carried out using, respectively, 20 μl of serum from patient No.3 and 10$^{12}$ virions derived from the amplification of the 2nd selection.

The 4th selection will use 20 μl of serum from patient No.4 and 10$^{12}$ virions derived from the amplification of the 3rd selection.

The 5th selection is carried out differently: 20 μl of a pool of 5 sera corresponding to patient Nos. 5, 6, 7, 8, 9, 10 are preincubated with 50 μl of wild-type phage for 8 hours at 4°

C. before being deposited in the Petri dish and incubated overnight at 4° C., with stirring, so as to be captured by the biotinylated human total antiimmunoglobulins. Moreover, 100 μl of the amplified phages after the 4th selection (about $10^{12}$ virions) were preincubated overnight at 4° C., with stirring, with 100 μl of a pool of 5 sera from healthy individuals (that is to say about 1.2 mg of total immunoglobulins). After 10 washes of the Petri dish with TBS/0.5% Tween, the preceding mixture: phages derived from the 4th selection and sera from healthy individuals is brought into contact, in the Petri dish, with the total immunoglobulins of the pool of patients. The immunoglobulins bound in the Petri dish and nonspecific to the patient will thus be in competition with a large excess of the same immunoglobulins present in the mixture to interact with the phages. Only the selection of the phages interacting with the immunoglobulins specific to the patient will be favored. After 10 new washes of the Petri dish, the phages bound are eluted and the eluate neutralized as described for the 1st selection.

10 μl of the $10^{-8}$ and $10^{-9}$ dilutions of the phages eluted above are each used to infect 10 μl of a suspension containing $5 \times 10^9$ bacteria/ml of the K91Kan strain. After incubating for 10 min at room temperature, 1 ml of NZY medium containing 0.2 μg of tetracycline are added for an additional incubation of 45 minutes at 37° C., with stirring. The suspensions of bacterial infected with the phages are then plated in Petri dishes (85 mm in diameter), on solid NZY medium containing 40 μg/ml of tetracycline and 100 μg/ml of kanamycin.

After incubating for 24 hours at 37° C., $10^8$ randomly chosen infected bacteria colonies are inoculated individually into 1.7 ml of NZY-tetracycline (20 μg/ml) medium. After culturing, with stirring, for 16 to 24 hours at 37° C., the cells are removed by centrifugation. The supernatant (1 ml) is mixed with 150 μl of a PEG/NaCl solution and incubated for four hours at 4° C. After centrifugation, the phages are resuspended in 500 μl of TBS.

The phage preparations thus obtained contain about $5 \times 10^{11}$ phages per milliliter.

EXAMPLE 2

Immunological Analysis of Said Clones by the ELISA Technique

Each clone is tested simultaneously for its IgG and IgM immunoreactivity with respect to a pool of 5 sera from healthy individuals and a pool of sera from patients suffering from multiple sclerosis at the remission stage. Each trial is carried out in triplicate.

In a first instance, 100 μl of anti-M13 phage antibodies diluted 1/500 in 0.1M $NaHCO_3$, pH 8.6 (marketed by Prinn, Inc. Boulder, Colo. 80303) are bound overnight in the wells of Nunc maxisorb (trade name) microtiter plates. After three washes with TBS/0.05% Tween, the plates are passivated for 1 hour at 37° C. with 250 μl of TBS containing 10% goat serum and again washed three times with the same buffer. 100 μl of various purified phage clones are then incubated for 2 hours at 37° C. in the wells. After three washes with TBS/0.05% Tween, 100 μl of a 1/50 dilution of serum are added and incubated for 2 hours at 37° C. After four washes in TBS/0.05% Tween, 100 μl of peroxidase-labeled anti-human IgG conjugate diluted 1/10,000 (marketed by Jackson Immuno Research Laboratories Inc.) are added before an incubation for one hour at 37° C. The enzymatic reaction for revealing is carried out by adding 100 μl of an $H_2O_2$/ortho-phenylenediamine (OPD) solution and incubating the sample for 30 minutes at room temperature. The staining reaction is interrupted by the addition of 50 μl of 1.8N sulfuric acid. The optical density is measured on a BioMérieux plate reader at 492 nm. The IgM response is determined by addition of 100 μl of biotinylated anti-IgM conjugate diluted 1/4000 (Biomérieux monoclonal antibody) followed by the addition, after the washes, of the streptavidin-peroxidase conjugate diluted 1/10,000. The revealing reaction is then carried out as described above.

The results obtained in ELISA are expressed by subtracting, for each clone, the mean of the values obtained with the pool of sera from healthy individuals from the mean of the values obtained with the pool of sera from patients. A positive response is thus obtained for 37 phage clones.

EXAMPLE 3

Determination of the Sequence of the Phage Clones Selected

The DNA of the phages corresponding to the 37 clones which gave a positive response in ELISA was prepared according to the method described by Sambrook et al., 1989. Molecular Cloning : A Laboratory Manual, 2nd Edition, Cold Spring Harbor Laboratory, Cold Spring Harbor.

These clones were sequenced using a prime of 20 bases (5'-CCCTCATAGTTAGCGTAACG-3') SEQ ID NO: 28. This primers is complementary to nucleotides 1717–1736 of the gene encoding the native PIII protein of the phage. The sequencing was carried out on an automated sequencer (Applied Biosystems, 373 A) using the "Prism ready reaction kit dye deoxyterminator cycle sequencing dye" according to the supplier's protocol (Applied Biosystems).

The nucleic sequences obtained, when they are converted to amino acid sequences, indicate that the peptide sequences SEQ ID NO: 3 (Leu Gln Gln Ala Val Phe) and SEQ ID NO: 4 (Ser Thr Gly Arg Pro Leu) are found 11 times and 6 times, respectively, in the clones selected for their positive response. Furthermore, as shown in the following table, other sequences are represented in duplicate or in triplicate.

Moreover, the sequence of the clones for which a negative response is observed does not possess any homology with these sequences.

The following Table 1 gives the IgG and IgM responses of the various phage clones expressing the sequences SEQ ID NOs: 3 to 9.

The results are expressed by subtracting, for each clone, the mean of the values obtained with the pool of sera from healthy individuals from the mean of the values obtained with the pool of sera from patients.

TABLE 1

| Peptide seq. | No. of clones | IgG rp | IgM rp |
| --- | --- | --- | --- |
| SEQ ID NO: 3 | 11 | 0.135 | 0 |
| LQQAVF | | 0.160 | 0.009 |
| | | 0.266 | 0 |
| | | 0.335 | 0.074 |
| | | 0.105 | 0.097 |
| | | 0.280 | 0.056 |
| | | 0.267 | 0.061 |
| | | 0.137 | 0.043 |
| | | 0.113 | 0.026 |
| | | 0.383 | 0.069 |
| | | 0.310 | 0.067 |

TABLE 1-continued

| Peptide seq. | No. of clones | IgG rp | IgM rp |
|---|---|---|---|
| SEQ ID NO: 4 | 6 | 0.264 | 0 |
| STGRPL | | 0.182 | 0.007 |
| | | 0.160 | 0 |
| | | 0.131 | 0.026 |
| | | 0.110 | 0.054 |
| | | 0.287 | 0.023 |
| SEQ ID NO: 5 | 2 | 0.185 | 0.068 |
| RLVLVP | | 0.366 | 0.012 |
| SEQ ID NO: 6 | 3 | 0.058 | 0.042 |
| FLENGV | | 0.016 | 0.042 |
| | | 0.020 | 0.044 |
| SEQ ID NO: 7 | 2 | 0.206 | 0.066 |
| KGTSLS | | 0.116 | 0.017 |
| SEQ ID NO: 8 | 1 | 0.119 | 0.506 |
| LAVRHD | | | |
| SEQ ID NO: 9 | 1 | 0.280 | 0.247 |
| TFDRRI | | | |

EXAMPLE 4

Chemical Synthesis of Two Pentadecapeptides and ELISA Test with Positive Human Sera Depending on the information obtained from the preceding examples, the hexapeptides SEQ ID NO: 3 and SEQ ID NO: 4 were synthesized and biotinylated according to the method described in Patent Application No. EP 93420183 with the following modifications: the peptide still bound to the resin is selectively deprotected at the N-terminal position. After overnight incubation with the biotin-NHS at 50% in DMF, the peptide is then cleaved from the resin and treated as described in the patent cited above.

These peptides were then tested in ELISA with respect to their reactivity towards several sera from multiple sclerosis patients and from healthy individuals.

The wells of a Maxisorb (trade name, Nunc) microtiter plate are saturated with 100 µl of a 50 mM NaHCO$_3$ solution, pH 9.6, containing 10 µg/ml of streptavidin for 2 hours at 37° C. The plate is washed with TBS/0.05% Tween 20 buffer. The wells are then saturated with 250 µl of wash buffer supplemented with 10% goat serum for 1 hour at 37° C. and then washed as described above.

The sera to be analyzed are diluted 1/100 in saturation buffer, supplemented with 0.05% Tween 20 and incubated for 2 hours at 37° C. After washing, a solution of peroxidase-labeled anti-human immunoglobulin G goat antibody conjugate (marketed by Jackson Immuno Research Laboratories Inc.) is added at the dilution of 1/10,000 and the plates are incubated for 1 hour at 37° C. After washes, the ortho-phenylenediamine (OPD) substrate is added and the reaction is stopped after 10 minutes by adding 50 µl of H$_2$SO$_4$. The optical density is read at 492 nm.

The IgM response is determined by addition of a 1/4000 solution of mouse monoclonal antibody anti-alkaline phosphatase-labeled human M immunoglobulin conjugate (bioMérieux Ac 5A10D5). After incubation at 37° C. for one hour the plate is again washed and the p-nitrophenyl phosphate substrate at 1 mg/ml in an M solution of diethanolamine, pH 9.8, containing 1 mM MgCl$_2$, is added. The reaction is stopped after 30 minutes by the addition of 50 µl of 3N sodium hydroxide solution. The optical density is read at 405 nm.

Figure 2:
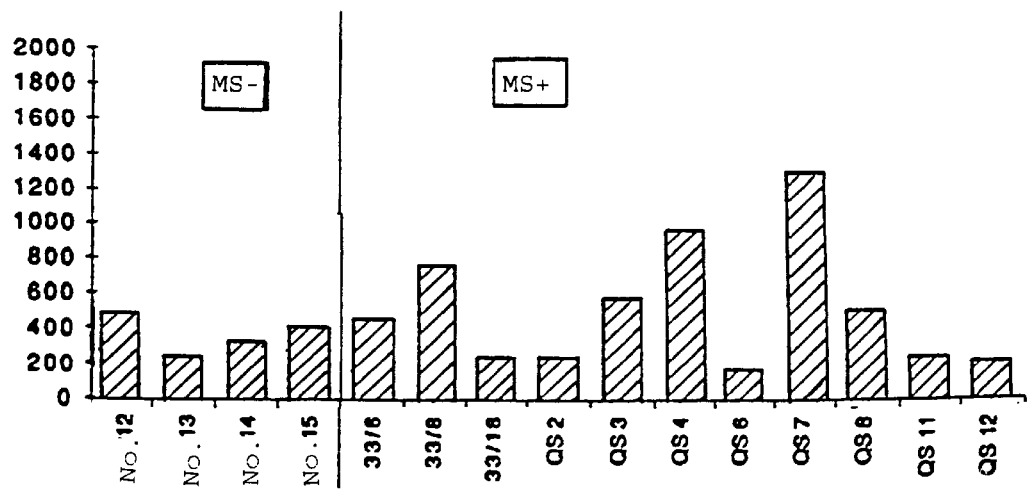
FIG. 2 represents the IgG response of the polypeptide SEQ ID NO: 4 with respect to human sera, on a histogram grouping together the results expressed in optical density values (×1000) and presented in Table 3 appended to the description; the polypeptide is tested in ELISA with respect to sera diluted 1/100; the MS– sera correspond to sera from healthy individuals; the MS+ sera correspond to sera from MS patients who have never been treated and who are all at the remission stage.

In a test carried out with 1/100 dilutions of 11 English sera from MS patients at the remission stage and 4 negative English sera, the peptides SEQ ID NOs: 3 and 4 are recognized by 4 sera out of 11 which give a positive IgG signal compared with the negative serum which gave the highest signal. If the mean of the values obtained with the negative sera is calculated and 3 times the standard deviation is added in order to determine a cut-off, the 2 peptides are still recognized significantly by 3 sera out of 11 (FIGS. 1 and 2).

The sequence SEQ ID NO: 3 has 4 consecutive and identical amino acids in the MSRV-1 region encoded by the LB19 clone (represented in FIG. 3). Likewise, the sequence SEQ ID NO: 4 has 4 consecutive and identical amino acids in the MSRV-1 region encoded by the GM3 clone (represented in FIG. 4).

The unit SEQ ID NO: 8 was found only once after sequencing, however, it gave a positive IgM response and exhibits sequence homology with HTLV1 gag. This unit was therefore also synthesized and biotinylated. The IgM response tested with respect to the same panel of sera described above shows that 7 sera out of 11 recognize this peptide (FIG. 5).

EXAMPLE 5

Selection of Pentadecapeptides Capable of Reacting Specifically with Sera from Patients Suffering from Multiple Sclerosis A library of pentadecapeptides carried on 300 copies of the phage protein VIII was constructed on the same principle as the hexapeptide library using the vector f88-4 according to the work by Greewood et al. (J. Biol. Mol. 1991). When f88-4 is propagated in the presence of IPTG, the foreign pentapeptide is expressed on the whole surface of the virion.

The same selection protocol as that described in Example 1 was used to screen this pentadecapeptide library with new remission sera.

After 5 biopannings, 72 phage clones were immunoanalyzed: 39 clones which gave a positive signal with respect to a pool of positive sera compared with a pool of negative sera were sequenced:

17/39 carry the sequence SEQ ID NO: 10: Asn Ala Cys Tyr Val Asp Leu Phe Leu Gly Ala Ser Val Cys Pro, these clones give an average positive IgG response of 0.069 with a 1/200 serum dilution 12/39 clones carry the sequence SEQ ID NO: 11: Ser Ser Ala Lys Ser His Cys Tyr Ala Phe Cys Ser Gly Leu Pro, with an average positive response of 0.248.

It should be noted that these 2 units both carry the amino acids Cys-Tyr. Furthermore, according to the BLAST program, SEQ ID NO: 11 shares 62% identity and 87% homology with the foot-and-mouth disease virus SAT3 protein.

Moreover, 2/39 clones carrying the sequence SEQ ID NO: 18 also have an average positive response of 0.358.

EXAMPLE 6

Selection of Pentadecapeptides Capable of Reacting Specifically with Cerebrospinal Fluids from Patients Suffering from Multiple Sclerosis The same pentadecapeptide library was targeted using the cerebrospinal fluids (CSF) from untreated patients suffering from multiple sclerosis, at the remission or chronic progressive phase. These CSFs were selected as a function of their oligoclonal profile by isoelectric focusing and of their IgG index, these two parameters showing an intrathecal synthesis of IgG.

In a protocol A, 4 biopannings were carried out with the CSFs from 4 different patients according. to the principle described in Example 1. 41 phage clones were then isolated and their DNA sequenced by automated sequencing using a primer of 20 bases (5'-TGAAGAGAGTCAAAAGCAGC-3') specific for protein VIII.

The units obtained are the following:

| | | |
|---|---|---|
| MPVSRLCIELDWCPP | 4/41 | SEQ ID NO: 12 |
| FCPPILPYSAWCPVP | 4/41 | SEQ ID NO: 13 |
| EPMTPHQWITLYRSY | 15/41 | SEQ ID NO: 14 |
| DTPYPWGWLLDEGYD | 9/41 | SEQ ID NO: 15 |
| RGTQEWTELWVSFRA | 2/41 | SEQ ID NO: 19 |

In parallel, in a protocol B, 4 successive biopannings were carried out using the same CSF (CSF 4 used for the first biopanning of protocol A) at increasing dilutions: 1, 1/10, 1/20 and 1/100.

32 phage clones derived from protocol B were also isolated and sequenced. The results show that the 2 units obtained with protocol A are also found with protocol B using a 1/100 dilution of CSF.

| | | |
|---|---|---|
| EPMTPHQWITLYRSY | 21/32 | SEQ ID NO: 14 |
| FCPPILPYSAWCPVP | 2/32 | SEQ ID NO: 13 |
| SRGSHEWAVLFRFYY | 3/32 | SEQ ID NO: 16 |
| RGTQEWTELWVSFRA | 2/32 | SEQ ID NO: 19 |
| QSPLEDRILRFLSPP | 2/32 | SEQ ID NO: 17 |

The phage clones carrying the sequences SEQ ID Nos: 13, 14, 16 and 17 as well as the nonrecombinant phage (that is to say not containing an inserted pentadecapeptide), were tested in ELISA with respect to a CSF from a neurological patient, CSF 4 (used in protocol B and the 1st biopanning of protocol A) and CSF 7 used for the 2nd biopanning of protocol A.

Figure 6:
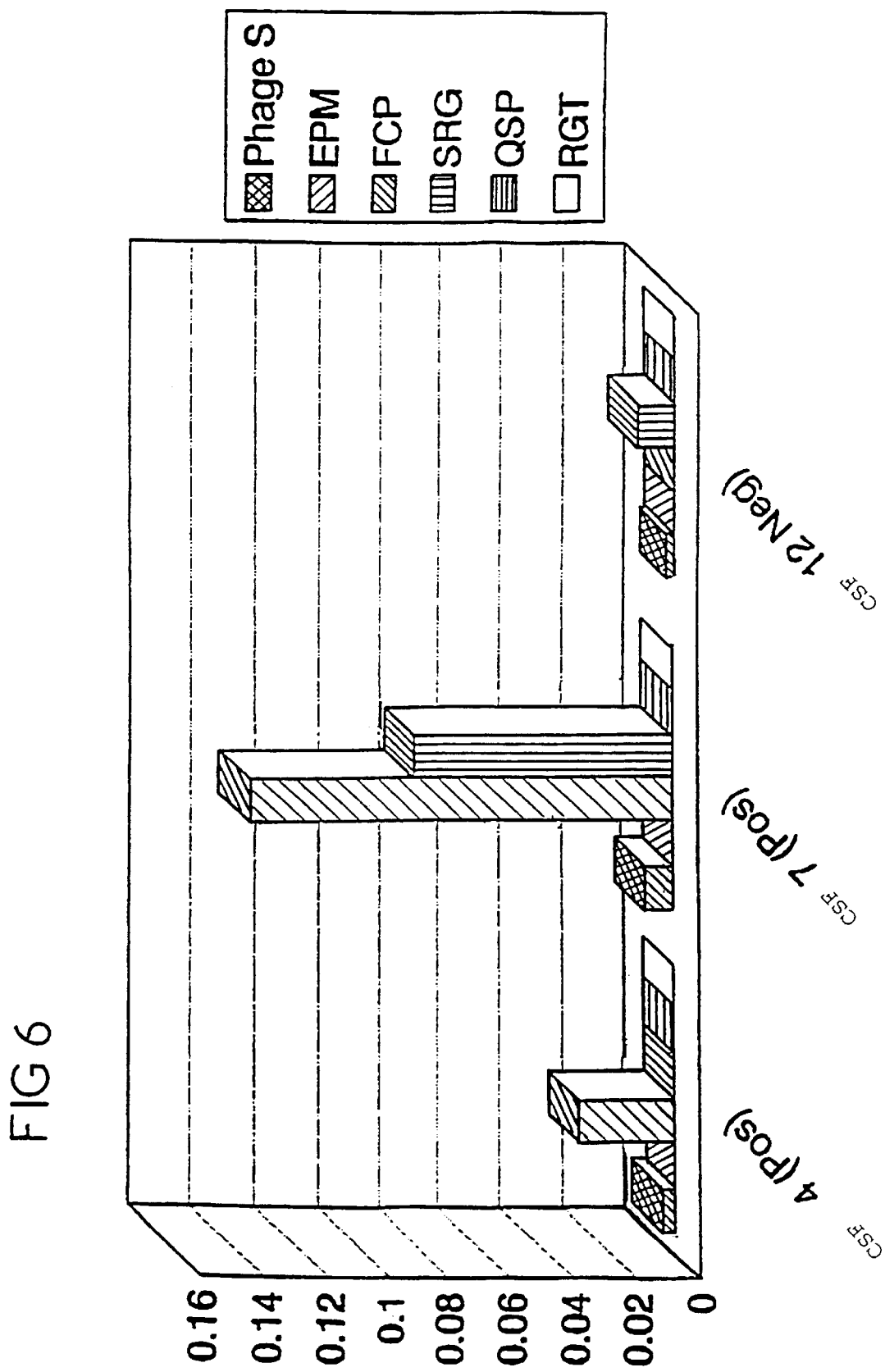
FIG. 6 represents the IgM response of the CSFs with respect to phages expressing the sequences SEQ ID NO: 14 (EPM), SEQ ID NO: 13 (FCP), SEQ ID NO: 16 (SRG), SEQ ID NO: 17 (QSP), with respect to the wild-type phage (without an expressed sequence) and another nonspecific sequence (RTG); this representation is given by a histogram grouping together the results expressed as optical density values obtained for each CSF reduced by those obtained with PBS buffer controls in place of the phages; the immunoreactivity of the phage clones is tested in ELISA as described in Example 2, with respect to CSFs diluted 1/10; CSF 12 corresponds to a patient suffering from a neurological disease other than MS; CSF 4 and CSF 7 correspond to two patients suffering from MS.

FIG. 6 shows that the sequence SEQ ID NO: 13 is recognized specifically by CSFs 7 and 4, whereas SEQ ID NO: 14 is recognized only by CSF 7. However, the predominant unit is not recognized by any of these two CSFs.

The sequence SEQ ID NO: 13 appears to be advantageous since, according to BLAST program, it shares 58% identity and 75% homology with the sequence p30/p10/5'v-fsm of the coding region of the feline sarcoma virus [NCBI reference gi/554646].

In a similar experiment, the pentadecapeptide library was screened in the same order of use with the sera obtained from patients whose CSFs were used above.

In a manner identical to Example 5, the sequences SEQ ID NO: 10 (18/36), SEQ ID NO: 11 (2/36) and SEQ ID NO: 18 (12/36) are again predominantly found. None of the other sequences selected corresponds to those selected by the CSFs and vice versa.

The difference in relative proportions of the clones compared with Example 5 may be explained by the fact that the sera used here are obtained from patients predominantly at a chronic stage of the disease whereas in Example 5 all the patients are at a remission stage.

Table 5, illustrated in FIGS. 7A and 7B, collates the results on the specific recognition of CSF from patients suffering from MS for 6 polypeptides of the invention, SEQ ID NO: 13, SEQ ID NO: 12, SEQ ID NO: 14, SEQ ID NO: 16, SEQ ID NO: 19 and SEQ ID NO: 15.

It is evident from Table 5 that the combination of the most immunoreactive polypeptides, namely SEQ ID NO: 12, SEQ ID NO: 13 and SEQ ID NO: 16, makes it possible to detect specific antibodies in 13 samples of CSF from patients suffering from MS out of 15.

TABLE 2

IGG RESPONSE TO THE BIOTINYLATED PEPTIDE L4F

| SERUM | OD 1 | OD 2 | OD 3 | MEAN | BASELINE |
|---|---|---|---|---|---|
| MS − | | | | | |
| Control 1 | 15 | 18 | 17 | 17 | 815 |
| No. 12 | 550 | 640 | 726 | 639 | |
| No. 13 | 366 | 369 | 407 | 377 | |
| No. 14 | 367 | 285 | 270 | 307 | |
| No. 15 | 439 | 496 | 422 | 452 | |
| MS + | | | | | |
| 33/6 | 535 | 599 | 626 | 587 | |
| 33/8 | 990 | 941 | 1271 | 1067 | X |
| 33/18 | 601 | 339 | 246 | 395 | |
| QS 2 | 294 | 339 | 293 | 309 | |
| QS 3 | 618 | 784 | 779 | 727 | |
| QS 4 | 1161 | 1293 | 1583 | 1346 | X |
| QS 6 | 306 | 263 | 407 | 325 | |
| QS 7 | 1307 | 1298 | 1461 | 1355 | X |
| QS 8 | 664 | 635 | 545 | 615 | |
| QS 11 | 429 | 169 | 108 | 235 | |
| QS 12 | 405 | 472 | 316 | 398 | |

TABLE 3

IGG RESPONSE TO THE BIOTINYLATED PEPTIDE S4L

| SERUM | OD 1 | OD 2 | OD 3 | MEAN | BASELINE |
|---|---|---|---|---|---|
| MS − | | | | | |
| Control 1 | 16 | 17 | 37 | 23 | 674 |
| No. 12 | 567 | 518 | 469 | 518 | |
| No. 13 | 286 | 278 | 268 | 271 | |
| No. 14 | 322 | 401 | 354 | 359 | |
| No. 15 | 423 | 432 | 470 | 442 | |
| MS + | | | | | |
| 33/6 | 465 | 496 | 525 | 496 | |
| 33/8 | 849 | 820 | 753 | 807 | X |
| 33/18 | 258 | 243 | 299 | 267 | |
| QS 2 | 267 | 296 | 267 | 277 | |
| QS 3 | 668 | 618 | 585 | 624 | |
| QS 4 | 1096 | 1120 | 862 | 1026 | X |
| QS 6 | 204 | 212 | 201 | 206 | |
| QS 7 | 1379 | 1437 | 1323 | 1380 | X |
| QS 8 | 523 | 504 | 630 | 552 | |
| QS 11 | 272 | 273 | 261 | 269 | |
| QS 12 | 271 | 227 | 212 | 237 | |

TABLE 4

IGM RESPONSE TO THE BIOTINYLATED PEPTIDE L4D

| SERUM | OD 1 | OD 2 | OD 3 | MEAN | MEAN | LINE |
|---|---|---|---|---|---|---|
| MS − | | | | | | |
| Control 1 | 213 | 170 | 136 | 173 | 173 | |
| No. 12 | 222 | 175 | 163 | 187 | 14 | |
| No. 13 | 145 | 154 | 196 | 165 | −6 | |
| No. 14 | 320 | 165 | 143 | 209 | 36 | |
| No. 15 | 254 | 205 | 173 | 211 | 38 | |

TABLE 4-continued

IGM RESPONSE TO THE BIOTINYLATED PEPTIDE L4D

| SERUM | OD 1 | OD 2 | OD 3 | MEAN | MEAN | LINE |
|---|---|---|---|---|---|---|
| | | | MS + | | | |
| 33/6 | 516 | 529 | 481 | 509 | 336 | X |
| 33/8 | 609 | 512 | 568 | 563 | 390 | X |
| 33/18 | 277 | 262 | 255 | 265 | 92 | X |
| QS 2 | 281 | 280 | 231 | 264 | 91 | X |
| QS 3 | 191 | 169 | 164 | 175 | 2 | |
| QS 4 | 374 | 361 | 346 | 360 | 187 | X |
| QS 6 | 156 | 147 | 151 | 151 | −22 | |
| QS 7 | 311 | 290 | 164 | 265 | 82 | X |
| QS 8 | 305 | 221 | 265 | 264 | 91 | X |
| QS 11 | 164 | 160 | 139 | 154 | −19 | |
| QS 12 | 123 | 57 | 148 | 109 | −64 | |

TABLE 5

| Patients | SEQ ID NO: 13 | SEQ ID NO: 12 | SEQ ID NO: 14 | SEQ ID NO: 16 | SEQ ID NO: 19 | SEQ ID NO: 15 |
|---|---|---|---|---|---|---|
| 1 | + | + | + | + | − | − |
| 2 | + | + | + | + | − | − |
| 3 | + | − | + | + | − | − |
| 5 | + | + | + | + | + | − |
| 6 | − | + | − | + | + | − |
| 7 | + | + | + | + | + | − |
| 8 | + | + | − | + | + | − |
| 10 | + | + | + | + | + | − |
| 16 | − | + | − | − | − | − |
| 17 | − | − | − | − | − | − |
| 18 | + | + | + | + | + | − |
| 19 | − | − | − | − | − | − |
| 20 | + | − | − | − | − | − |
| 21 | + | + | + | + | + | − |
| 22 | − | − | − | + | + | − |
| 15 | 10+ | 10+ | 8+ | 11+ | 8+ | 0+ |

For each polypeptide tested, identified in Table 5 by its peptide sequence, the CSFs from patients 1–22 suffering from Ms are determined as positive (+) if the OD value at 492 nm for a 1/10 dilution of the CSF is greater than the mean values obtained for the CSFs from the ND patients+3 times the standard deviation.

---

What is claimed is:

1. Polypeptide capable of reacting specifically with the antibodies of patients suffering from multiple sclerosis (MS) and whose peptide sequence comprises at least one sequence chosen from SEQ ID NO: 1, SEQ ID NO: 3, SEQ ID NO: 4, SEQ ID NO: 8, SEQ ID NO: 12 to SEQ ID NO: 14, SEQ ID NO: 16 and SEQ ID NO: 19, said polypeptide having no more than 20 amino acids.

2. Polypeptide of claim 1, said polypeptide having no more than 15 amino acids.

3. Reagent for the detection of multiple sclerosis in a patient and/or the monitoring of a patient suffering from multiple sclerosis, characterized in that it comprises at least one polypeptide according to claim 1, said polypeptide being optionally labeled.

4. Reagent according to claim 3, characterized in that it comprises at least two different polypeptides.

5. Polynucleotide whose nucleotide sequence encodes a polypeptide according to claim 1.

6. Polypeptide capable of reacting with the antibodies of patients suffering from multiple sclerosis (MS) and whose peptide sequence consists of a sequence selected from SEQ ID NO: 1, SEQ ID NO: 3, SEQ ID NO: 4, SEQ ID NO: 8, SEQ ID NO: 12 to SEQ ID NO: 14, SEQ ID NO: 16 and SEQ ID NO: 19.

7. Polypeptide capable of reacting with at least one antibody in at least one biological fluid from a patient in whom the MSRV-1 viral sequences have been detected and whose peptide sequence comprises at least one sequence chosen from SEQ ID NO: 1, SEQ ID NO: 3, SEQ ID NO: 4, said polypeptide having no more than 20 amino acids.

8. Polypeptide of claim 7, said polypeptide having no more than 15 amino acids.

9. Reagent for the detection of an MSRV-1 virus infection, characterized in that it comprises at least one polypeptide according to claim 7, said polypeptide being optionally labeled.

10. Polypeptide capable of reacting with at least one antibody in at least one biological fluid from a patient in whom MSRV-1 viral sequences have been detected and whose peptide sequence consists of a sequence chosen from SEQ ID NO: 1, SEQ ID NO: 3, SEQ ID NO: 4.

11. Kit for the detection of multiple sclerosis in a patient and/or the monitoring of a patient suffering from multiple sclerosis, comprising:

a reagent for the detection of multiple sclerosis in a patient and/or the monitoring of a patient suffering from multiple sclerosis, the reagent comprising at least one polypeptide capable of reacting specifically with the antibodies of patients suffering from multiple sclerosis (MS) and whose peptide sequence comprises at least one sequence chosen from SEQ ID NO: 1, SEQ ID NO: 3, SEQ ID NO: 4, SEQ ID NO: 8; SEQ ID NO: 12 to SEQ ID NO: 14, SEQ ID NO: 16 and SEQ ID NO: 19;

the polypeptide having no more than 20 amino acids; and the polypeptide being optionally labeled wherein the reagent is supported on a support which is immunologically compatible with said reagent.

12. Kit for the detection of an MSRV-1 virus infection, comprising:

a reagent for the detection of an MSRV-1 virus infection;

the reagent comprising at least one polypeptide capable of reacting with at least one biological fluid from a patient in whom the MSRV-1 viral sequences have been detected and whose peptide sequence comprises at least one sequence chosen from SEQ ID NO: 1 to SEQ ID NO: 4;

the polypeptide having no more than 20 amino acids; and the polypeptide being optionally labeled;

wherein the reagent is supported on a support which is immunologically compatible with said reagent.

13. Method of binding, in a biological sample, antibodies which are characteristic of and/or specific to multiple sclerosis, comprising:

bringing the sample into contact with a reagent for the detection of multiple sclerosis in a patient and/or the monitoring of a patient suffering from multiple sclerosis, the reagent comprising at least one polypeptide capable of reacting specifically with the antibodies of patients suffering from multiple sclerosis (MS) and whose peptide sequence comprises at least one sequence chosen from SEQ ID NO: 1, SEQ ID NO: 3, SEQ ID NO: 4, SEQ ID NO: 8, SEQ ID NO: 12 to SEQ ID NO: 14, SEQ ID NO: 16 and SEQ ID NO: 19;

the polypeptide having no more than 20 amino acids; and the polypeptide being optionally labeled;

optionally detecting the presence of an immune complex; and optionally separating the detected immune complex.

14. Method according to claim 13, characterized in that the biological sample is chosen from serum, cerebrospinal fluid and urine.

15. Method of binding, in a biological sample, antibodies directed against the MSRV-1 virus, comprising:

bringing the sample into contact with a reagent for the detection of an MSRV-1 virus infection;

the reagent comprising at least one polypeptide capable of reacting with at least one biological fluid from a patient in whom the MSRV-1 viral sequences have been detected and whose peptide sequence comprises at least one sequence chosen from SEQ ID NO: 1 to SEQ ID NO: 4;

the polypeptide having no more than 20 amino acids; and the polypeptide being optionally labeled;

optionally detecting the presence of an immune complex; and optionally separating the detected immune complex.

16. Kit for the detection of multiple sclerosis in a patient and/or the monitoring of a patient suffering from multiple sclerosis, comprising:

a reagent for the detection of multiple sclerosis in a patient and/or the monitoring of a patient suffering from multiple sclerosis;

the reagent comprising at least one polypeptide capable of reacting specifically with the antibodies of patients suffering from multiple sclerosis (MS) and whose peptide sequence comprises at least one sequence chosen from SEQ ID NO: 1, SEQ ID NO: 3, SEQ ID NO: 4, SEQ ID NO: 8, SEQ ID NO: 12 to SEQ ID NO: 14, SEQ ID NO: 16 and SEQ ID NO: 19;

the polypeptide having no more than 20 amino acids; and the polypeptide being optionally labeled;

wherein the reagent is supported on a support that does not react with the reagent.

17. Kit for the detection of an MSRV-1 virus infection, comprising:

a reagent for the detection of an MSRV-1 virus infection;

the reagent comprising at least one polypeptide capable of reacting with at least one biological fluid from a patient in whom the MSRV-1 viral sequences have been detected and whose peptide sequence comprises at least one sequence chosen from SEQ ID NO: 1 to SEQ ID NO: 4;

the polypeptide having no more than 20 amino acids; and the polypeptide being optionally labeled;

wherein the reagent is supported on a support that does not react with the reagent.

* * * * *

SEQUENCE LISTING

<160> NUMBER OF SEQ ID NOS: 34

<210> SEQ ID NO 1
<211> LENGTH: 4
<212> TYPE: PRT
<213> ORGANISM: MSRV

<400> SEQUENCE: 1

Gln Gln Ala Val
 1

<210> SEQ ID NO 2
<211> LENGTH: 4
<212> TYPE: PRT
<213> ORGANISM: MSRV

<400> SEQUENCE: 2

Thr Gly Arg Pro
 1

<210> SEQ ID NO 3
<211> LENGTH: 6
<212> TYPE: PRT
<213> ORGANISM: MSRV

<400> SEQUENCE: 3

Leu Gln Gln Ala Val Phe
 1               5

<210> SEQ ID NO 4
<211> LENGTH: 6
<212> TYPE: PRT
<213> ORGANISM: MSRV

<400> SEQUENCE: 4

Ser Thr Gly Arg Pro Leu

-continued

```
          1               5

<210> SEQ ID NO 5
<211> LENGTH: 6
<212> TYPE: PRT
<213> ORGANISM: MSRV

<400> SEQUENCE: 5

Arg Leu Val Leu Val Pro
 1               5

<210> SEQ ID NO 6
<211> LENGTH: 6
<212> TYPE: PRT
<213> ORGANISM: MSRV

<400> SEQUENCE: 6

Phe Leu Glu Asn Gly Val
 1               5

<210> SEQ ID NO 7
<211> LENGTH: 6
<212> TYPE: PRT
<213> ORGANISM: MSRV

<400> SEQUENCE: 7

Lys Gly Thr Ser Leu Ser
 1               5

<210> SEQ ID NO 8
<211> LENGTH: 6
<212> TYPE: PRT
<213> ORGANISM: MSRV

<400> SEQUENCE: 8

Leu Ala Val Arg His Asp
 1               5

<210> SEQ ID NO 9
<211> LENGTH: 6
<212> TYPE: PRT
<213> ORGANISM: MSRV

<400> SEQUENCE: 9

Thr Phe Asp Arg Arg Ile
 1               5

<210> SEQ ID NO 10
<211> LENGTH: 15
<212> TYPE: PRT
<213> ORGANISM: MSRV

<400> SEQUENCE: 10

Asn Ala Cys Tyr Val Asp Leu Phe Leu Gly Ala Ser Val Cys Pro
 1               5                  10                  15

<210> SEQ ID NO 11
<211> LENGTH: 15
<212> TYPE: PRT
<213> ORGANISM: MSRV

<400> SEQUENCE: 11

Ser Ser Ala Lys Ser His Cys Tyr Ala Phe Cys Ser Gly Leu Pro
 1               5                  10                  15
```

<210> SEQ ID NO 12
<211> LENGTH: 15
<212> TYPE: PRT
<213> ORGANISM: MSRV

<400> SEQUENCE: 12

Met Pro Val Ser Arg Leu Cys Ile Glu Leu Asp Trp Cys Pro Pro
1               5                   10                  15

<210> SEQ ID NO 13
<211> LENGTH: 15
<212> TYPE: PRT
<213> ORGANISM: MSRV

<400> SEQUENCE: 13

Phe Cys Pro Pro Ile Leu Pro Tyr Ser Ala Trp Cys Pro Val Pro
1               5                   10                  15

<210> SEQ ID NO 14
<211> LENGTH: 15
<212> TYPE: PRT
<213> ORGANISM: MSRV

<400> SEQUENCE: 14

Glu Pro Met Thr Pro His Gln Trp Ile Thr Leu Tyr Arg Ser Tyr
1               5                   10                  15

<210> SEQ ID NO 15
<211> LENGTH: 15
<212> TYPE: PRT
<213> ORGANISM: MSRV

<400> SEQUENCE: 15

Asp Thr Pro Tyr Pro Trp Gly Trp Leu Leu Asp Glu Gly Tyr Asp
1               5                   10                  15

<210> SEQ ID NO 16
<211> LENGTH: 15
<212> TYPE: PRT
<213> ORGANISM: MSRV

<400> SEQUENCE: 16

Ser Arg Gly Ser His Glu Trp Ala Val Leu Phe Arg Phe Tyr Tyr
1               5                   10                  15

<210> SEQ ID NO 17
<211> LENGTH: 15
<212> TYPE: PRT
<213> ORGANISM: MSRV

<400> SEQUENCE: 17

Gln Ser Pro Leu Glu Asp Arg Ile Leu Arg Phe Leu Ser Pro Pro
1               5                   10                  15

<210> SEQ ID NO 18
<211> LENGTH: 15
<212> TYPE: PRT
<213> ORGANISM: MSRV

<400> SEQUENCE: 18

His Cys Arg Lys Val Thr Gly Ser Asp Tyr Leu Leu Cys Gly Leu
1               5                   10                  15

<210> SEQ ID NO 19

```
<211> LENGTH: 15
<212> TYPE: PRT
<213> ORGANISM: MSRV

<400> SEQUENCE: 19

Arg Gly Thr Gln Glu Trp Thr Glu Leu Trp Val Ser Phe Arg Ala
 1               5                  10                  15

<210> SEQ ID NO 20
<211> LENGTH: 565
<212> TYPE: PRT
<213> ORGANISM: MSRV

<400> SEQUENCE: 20

Met Lys Met Arg Pro Arg Tyr Ser Val Ile Ala Ser Ala Val Ser Leu
 1               5                  10                  15

Gly Phe Val Leu Ser Lys Ser Val Met Ala Leu Gly Gln Pro Asp Thr
                20                  25                  30

Gly Ser Leu Asn Arg Glu Leu Glu Gln Arg Gln Ile Gln Ser Glu Ala
            35                  40                  45

Lys Pro Ser Gly Glu Leu Phe Asn Gln Thr Ala Asn Ser Pro Tyr Thr
50                  55                  60

Ala Gln Tyr Lys Gln Gly Leu Lys Phe Pro Leu Thr Gln Val Gln Ile
65                  70                  75                  80

Leu Asp Arg Asn Asn Gln Glu Val Val Thr Asp Glu Leu Ala His Ile
                85                  90                  95

Leu Lys Asn Tyr Val Gly Lys Glu Val Ser Leu Ser Asp Leu Ser Asn
            100                 105                 110

Leu Ala Asn Glu Ile Ser Glu Phe Tyr Arg His Asn Asn Tyr Leu Val
        115                 120                 125

Ala Lys Ala Ile Leu Pro Pro Gln Glu Ile Glu Gln Gly Thr Val Lys
130                 135                 140

Ile Leu Leu Leu Lys Gly Asn Val Gly Glu Ile Arg Leu Gln Asn His
145                 150                 155                 160

Ser Ala Leu Ser Asn Lys Phe Val Ser Arg Leu Ser Asn Thr Thr Val
                165                 170                 175

Asn Thr Ser Glu Phe Ile Leu Lys Asp Glu Leu Glu Lys Phe Ala Leu
            180                 185                 190

Thr Ile Asn Asp Val Pro Gly Val Asn Ala Gly Leu Gln Leu Ser Ala
        195                 200                 205

Gly Lys Lys Val Gly Glu Ala Asn Leu Leu Ile Lys Ile Asn Asp Ala
210                 215                 220

Lys Arg Phe Ser Ser Tyr Val Ser Val Asp Asn Gln Gly Asn Lys Tyr
225                 230                 235                 240

Thr Gly Arg Tyr Arg Leu Ala Ala Gly Thr Lys Val Ser Asn Leu Asn
                245                 250                 255

Gly Trp Gly Asp Glu Leu Lys Leu Asp Leu Met Ser Ser Asn Gln Ala
            260                 265                 270

Asn Leu Lys Asn Ala Arg Ile Asp Tyr Ser Ser Leu Ile Asp Gly Tyr
        275                 280                 285

Ser Thr Arg Phe Gly Val Thr Ala Asn Tyr Leu Asp Tyr Lys Leu Gly
290                 295                 300

Gly Asn Phe Lys Ser Leu Gln Ser Gln Gly His Ser His Thr Leu Gly
305                 310                 315                 320

Ala Tyr Leu Leu His Pro Thr Ile Arg Thr Pro Asn Phe Arg Leu Ser
                325                 330                 335
```

-continued

```
Thr Lys Val Ser Phe Asn His Gln Asn Leu Thr Asp Lys Gln Gln Ala
            340                 345                 350

Val Tyr Val Lys Gln Lys Arg Lys Ile Asn Ser Leu Thr Ala Gly Ile
        355                 360                 365

Asp Gly Ser Trp Asn Leu Ile Lys Asp Gly Thr Thr Tyr Phe Ser Leu
    370                 375                 380

Ser Thr Leu Phe Gly Asn Leu Ala Asn Gln Thr Ser Glu Lys Lys His
385                 390                 395                 400

Asn Ala Val Glu Asn Phe Gln Pro Lys Ser His Phe Thr Val Tyr Asn
                405                 410                 415

Tyr Arg Leu Ser His Glu Gln Ile Leu Pro Lys Ser Phe Ala Phe Asn
            420                 425                 430

Ile Gly Ile Asn Gly Gln Phe Ala Asp Lys Thr Leu Glu Ser Ser Gln
        435                 440                 445

Lys Met Leu Leu Gly Gly Leu Ser Gly Val Arg Gly His Gln Ala Gly
    450                 455                 460

Ala Ala Ser Val Asp Glu Gly His Leu Ile Gln Thr Glu Phe Lys His
465                 470                 475                 480

Tyr Leu Pro Val Phe Ser Gln Ser Val Leu Val Ser Ser Leu Phe Tyr
                485                 490                 495

Asp Tyr Gly Leu Gly Lys Tyr Tyr Lys Asn Ser Gln Phe Leu Glu Gln
            500                 505                 510

Gly Val Lys Asn Ser Val Lys Leu Gln Ser Val Gly Ala Gly Leu Ser
        515                 520                 525

Leu Ser Asp Ala Gly Ser Tyr Ala Ile Asn Val Ser Val Ala Lys Pro
    530                 535                 540

Leu Asp Asn Asn Ile Asn Asn Ala Asp Lys His Gln Phe Trp Leu Ser
545                 550                 555                 560

Met Ile Lys Thr Phe
            565

<210> SEQ ID NO 21
<211> LENGTH: 359
<212> TYPE: PRT
<213> ORGANISM: MSRV

<400> SEQUENCE: 21

Met Ala Lys Leu Leu Asp Ile Val Lys Pro Gly Val Val Thr Gly Glu
  1               5                  10                  15

Asp Val Gln Lys Val Phe Ala Tyr Ala Lys Glu His Asn Phe Ala Ile
                20                  25                  30

Pro Ala Val Asn Cys Val Gly Ser Asp Ser Val Asn Ala Val Leu Glu
            35                  40                  45

Thr Ala Ala Arg Val Lys Ala Pro Val Ile Ile Gln Phe Ser Asn Gly
        50                  55                  60

Gly Ala Ala Phe Tyr Ala Gly Lys Gly Ile Lys Pro Thr Ser Gly Thr
65                  70                  75                  80

Arg Pro Asp Val Leu Gly Ala Ile Ala Gly Ala Lys Gln Val His Thr
                85                  90                  95

Leu Ala Lys Glu Tyr Gly Val Pro Val Ile Leu His Thr Asp His Ala
            100                 105                 110

Ala Lys Lys Leu Leu Pro Trp Ile Asp Gly Leu Leu Asp Ala Gly Glu
        115                 120                 125

Lys His Phe Ala Glu Thr Gly Arg Pro Leu Phe Ser Ser His Met Ile
```

```
                130                 135                 140
Asp Leu Ser Glu Glu Ser Met Glu Glu Asn Met Ala Ile Cys Arg Glu
145                 150                 155                 160

Tyr Leu Ala Arg Met Asp Lys Met Gly Met Thr Leu Glu Ile Glu Ile
                165                 170                 175

Gly Ile Thr Gly Gly Glu Glu Asp Gly Val Asp Asn Ser Asp Val Asp
                180                 185                 190

Glu Ser Arg Leu Tyr Thr Gln Pro Ser Asp Val Leu Tyr Val Tyr Asp
                195                 200                 205

Gln Leu His Pro Val Ser Pro Asn Phe Thr Val Ala Ala Ala Phe Gly
            210                 215                 220

Asn Val His Gly Val Tyr Lys Pro Gly Asn Val Lys Leu Lys Pro Ser
225                 230                 235                 240

Ile Leu Gly Glu Ser Gln Glu Phe Val Ser Lys Glu Arg Asn Leu Pro
                245                 250                 255

Ala Lys Pro Ile Asn Phe Val Phe His Gly Ser Gly Ser Ser Arg
                260                 265                 270

Glu Glu Ile Arg Glu Ala Ile Gly Tyr Gly Ala Ile Lys Met Asn Ile
                275                 280                 285

Asp Thr Asp Thr Gln Trp Ala Ser Trp Asn Gly Ile Leu Asn Phe Tyr
                290                 295                 300

Lys Ala Asn Glu Ala Tyr Leu Gln Gly Gln Leu Gly Asn Pro Glu Gly
305                 310                 315                 320

Pro Asp Ala Pro Asn Lys Lys Tyr Tyr Asp Pro Arg Val Trp Leu Arg
                325                 330                 335

Lys Met Glu Glu Ser Met Ser Lys Arg Leu Glu Gln Ser Phe Glu Asp
                340                 345                 350

Leu Asn Cys Val Asp Val Leu
            355

<210> SEQ ID NO 22
<211> LENGTH: 304
<212> TYPE: PRT
<213> ORGANISM: MSRV

<400> SEQUENCE: 22

Met Thr Lys Met Lys Gln Met Leu Ile Cys Ile Leu Cys Gly His Leu
1               5                   10                  15

Cys Ile Thr Trp Ile Gln Met Met Cys Gly Ile Arg Gln Gln Val Gly
                20                  25                  30

Ser Ile Lys Leu Ala Phe Thr Thr Tyr Met Glu His Leu Asn Thr Ile
            35                  40                  45

Met Cys Tyr Leu Leu Met Met Gln Arg Asp Ile Val Leu Leu Glu Asn
        50                  55                  60

Gly Lys Leu Lys Leu Ile Arg Lys Leu Cys Leu Leu Ser Leu Ala
65                  70                  75                  80

Pro His His Gln Gly His Gln Glu Asp Lys Gln Thr Gln Thr Pro Pro
                85                  90                  95

Pro Arg Pro Pro Pro Pro Gln Pro Pro Leu Thr Pro Arg Pro Asp
                100                 105                 110

Ala Asn Pro Ser Ile Asn Ser His Asn Lys Pro Lys Pro Asn Glu Glu
            115                 120                 125

Gly Thr Asp Gly Asp His Gln Ala Glu Gln Gly Asp Arg Lys Arg Thr
130                 135                 140
```

-continued

```
Lys Gly Asp Pro Asp Pro Asp Pro Gly Arg Gly Pro Val Leu Lys Pro
145                 150                 155                 160

Thr Leu Pro Pro Pro Pro Pro Pro Pro Pro Thr Gly Pro Gly Leu Arg
                165                 170                 175

Arg Ser Thr Arg Leu Val Leu Val Pro Gly Gln Gly Pro Pro Pro Asp
            180                 185                 190

Leu Pro Ala Pro Pro Val Glu Gly Glu Val Glu Gly His Pro Gln Gly
        195                 200                 205

Lys Asp Arg Asp His Pro Pro Pro Thr Pro Gln Asn Gly His Gly Lys
    210                 215                 220

Glu Thr Gln Gly Ala Glu Gly Gly Gly Asp Gln Gly Glu Gln Gly Ala
225                 230                 235                 240

Val Gly Gly Glu Ser Ser Asp Gly Glu Gly Asp His Ser Gln Pro Pro
                245                 250                 255

Leu Thr Pro Pro Asn Glu Ser Asp Gly Ser Leu Leu Asn Thr Val Ala
            260                 265                 270

Cys Leu Leu Ala Arg Trp Glu Ser Asn Phe Asp Gln Leu Val Gln Asn
        275                 280                 285

Ile Gln Gly Asp Leu Glu Gly Tyr Trp Arg Lys Leu Gly Thr Pro Gln
    290                 295                 300

<210> SEQ ID NO 23
<211> LENGTH: 425
<212> TYPE: PRT
<213> ORGANISM: MSRV

<400> SEQUENCE: 23

Met Arg Gln Val Ala Tyr Arg Arg Arg Arg Glu Ser Ser Cys Ala Val
  1               5                  10                  15

Leu Val His His Val Gly Arg Asp Gly Asp Gly Glu Gly Glu Ala Ala
             20                  25                  30

Lys Lys Thr Cys Lys Lys Thr Gly Arg Ser Val Ala Gly Ile Pro Gly
         35                  40                  45

Glu Lys Leu Arg Arg Thr Val Val Thr Thr Thr Pro Ala Arg Arg Leu
     50                  55                  60

Ser Gly Arg His Thr Glu Gln Glu Gln Ala Gly Met Arg Leu Cys Glu
 65                  70                  75                  80

Lys Gly Lys Lys Arg Ile Ile Met Cys Arg Arg Glu Ser Leu Arg Thr
                 85                  90                  95

Leu Pro Trp Leu Phe Trp Val Leu Leu Ser Cys Pro Arg Leu Leu Glu
            100                 105                 110

Tyr Ser Ser Ser Ser Phe Pro Phe Ala Thr Ala Asp Ile Ala Glu Lys
        115                 120                 125

Met Trp Ala Glu Asn Tyr Glu Thr Thr Ser Pro Ala Pro Val Leu Val
    130                 135                 140

Ala Glu Gly Glu Gln Val Thr Ile Pro Cys Thr Val Met Thr His Ser
145                 150                 155                 160

Trp Pro Met Val Ser Ile Arg Ala Arg Phe Cys Arg Ser His Asp Gly
                165                 170                 175

Ser Asp Glu Leu Ile Leu Asp Ala Val Lys Gly His Arg Leu Met Asn
            180                 185                 190

Gly Leu Gln Tyr Arg Leu Pro Tyr Ala Thr Trp Asn Phe Ser Gln Leu
        195                 200                 205

His Leu Gly Gln Ile Phe Ser Leu Thr Phe Asn Val Ser Met Asp Thr
    210                 215                 220
```

-continued

```
Ala Gly Met Tyr Glu Cys Val Leu Arg Asn Tyr Ser His Gly Leu Ile
225                 230                 235                 240

Met Gln Arg Phe Val Ile Leu Thr Gln Leu Glu Thr Leu Ser Arg Pro
            245                 250                 255

Asp Glu Pro Cys Cys Thr Pro Ala Leu Gly Arg Tyr Ser Leu Gly Asp
            260                 265                 270

Gln Ile Trp Ser Pro Thr Pro Trp Arg Leu Arg Asn His Asp Cys Gly
            275                 280                 285

Thr Tyr Arg Gly Phe Gln Arg Asn Tyr Phe Tyr Ile Gly Arg Ala Asp
        290                 295                 300

Ala Glu Asp Cys Trp Lys Pro Ala Cys Pro Asp Glu Pro Asp Arg
305                 310                 315                 320

Cys Trp Thr Val Ile Gln Arg Tyr Arg Leu Pro Gly Asp Cys Tyr Arg
                325                 330                 335

Ser Gln Pro His Pro Pro Lys Phe Leu Pro Val Thr Pro Ala Pro Pro
            340                 345                 350

Ala Asp Ile Asp Thr Gly Met Ser Pro Trp Ala Thr Arg Gly Ile Ala
            355                 360                 365

Ala Phe Leu Gly Phe Trp Ser Ile Phe Thr Val Cys Phe Leu Cys Tyr
        370                 375                 380

Leu Cys Tyr Leu Gln Cys Cys Gly Arg Trp Cys Pro Thr Pro Gly Arg
385                 390                 395                 400

Gly Arg Arg Gly Gly Glu Gly Tyr Arg Arg Leu Pro Thr Tyr Asp Ser
                405                 410                 415

Tyr Pro Gly Val Arg Lys Met Lys Arg
            420                 425

<210> SEQ ID NO 24
<211> LENGTH: 96
<212> TYPE: PRT
<213> ORGANISM: MSRV

<400> SEQUENCE: 24

Tyr Leu Arg His Thr Glu Glu Tyr Glu Val Glu Leu Ile Leu Arg Leu
1               5                   10                  15

Cys Lys Val Pro Leu Asn Pro Asp Val Leu Ala His Leu Asn Val Met
            20                  25                  30

Asp Lys Asn Ile Leu Glu Asp Trp Gln Leu Ser Phe Val Pro Pro Pro
        35                  40                  45

Pro Gln Gly Ile Glu Asp Ala Tyr Arg Tyr Ile Met Ser Gln Ala Thr
    50                  55                  60

Met Cys Pro Thr Asp Val Pro Asn Thr Glu Arg Glu Asp Pro Tyr Lys
65                  70                  75                  80

Gln Tyr Thr Phe Trp Thr Ile Asp Leu Gln Glu Arg Phe Ser Asn Glu
                85                  90                  95

<210> SEQ ID NO 25
<211> LENGTH: 64
<212> TYPE: PRT
<213> ORGANISM: MSRV

<400> SEQUENCE: 25

Gly Arg Asp Gly Tyr Ile Val Asp Ser Lys Asn Cys Val Tyr His Cys
1               5                   10                  15

Tyr Pro Pro Cys Asp Gly Leu Cys Lys Lys Asn Gly Ala Lys Ser Gly
            20                  25                  30
```

```
Ser Cys Gly Phe Leu Val Pro Ser Gly Leu Ala Cys Trp Cys Asn Asp
        35                  40                  45

Leu Pro Glu Asn Val Pro Ile Lys Asp Pro Ser Asp Cys His Lys
    50                  55                  60

<210> SEQ ID NO 26
<211> LENGTH: 9
<212> TYPE: PRT
<213> ORGANISM: MSRV

<400> SEQUENCE: 26

Lys Arg Asp Ser Ile Ser Pro Tyr Ser
  1               5

<210> SEQ ID NO 27
<211> LENGTH: 9
<212> TYPE: PRT
<213> ORGANISM: MSRV

<400> SEQUENCE: 27

Arg Arg Asp Thr Ile Ser Pro Tyr Ser
  1               5

<210> SEQ ID NO 28
<211> LENGTH: 20
<212> TYPE: DNA
<213> ORGANISM: Unknown Organism
<220> FEATURE:
<223> OTHER INFORMATION: Description of Unknown Organism:  Primer

<400> SEQUENCE: 28
ccctcatagt tagcgtaacg                                              20

<210> SEQ ID NO 29
<211> LENGTH: 19
<212> TYPE: PRT
<213> ORGANISM: Unknown Organism
<220> FEATURE:
<221> NAME/KEY: CHAIN
<222> LOCATION: (5)..(10)
<223> OTHER INFORMATION: Hexapeptide from Phage Library
<220> FEATURE:
<223> OTHER INFORMATION: Description of Unknown Organism: Hexapeptide
      from Phage Library

<400> SEQUENCE: 29

Ala Asp Gly Ala Xaa Xaa Xaa Xaa Xaa Xaa Gly Ala Ala Gly Ala Glu
  1               5                  10                  15

Thr Val Glu

<210> SEQ ID NO 30
<211> LENGTH: 498
<212> TYPE: DNA
<213> ORGANISM: MSRV

<400> SEQUENCE: 30
ctccttcccc aactaataag gacccccctt tcaacccaaa cagtccaaaa ggacatagac      60
aaaggagtaa acaatgaacc aaagagtgcc aatattccct ggttatgcac cctccaagcg    120
gtgggagaag aattcggccc agccagagtg catgtacctt tttctctctc acacttgaag    180
caaattaaaa tagacctagg taaattctca gatagccctg atggctatat tgatgtttta    240
caaggattag gacaatcctt tgatctgaca tggagagata taatattact gctaaatcag    300
```

```
acgctaacct caaatgagag aagtgctgcc ataactggag cccgagagtt tggcaatctc    360
tggtatctca gtcaggtcaa tgataggatg acaacggagg aaagagaacg attccccaca    420
gggcagcagg cagttcccag tgtagctcct cattgggaca cagaatcaga acatggagat    480
tggtgccgca gacattta                                                  498
```

<210> SEQ ID NO 31
<211> LENGTH: 166
<212> TYPE: PRT
<213> ORGANISM: MSRV

<400> SEQUENCE: 31

```
Leu Leu Pro Gln Leu Ile Arg Thr Pro Leu Ser Thr Gln Thr Val Gln
 1               5                  10                  15

Lys Asp Ile Asp Lys Gly Val Asn Asn Glu Pro Lys Ser Ala Asn Ile
            20                  25                  30

Pro Trp Leu Cys Thr Leu Gln Ala Val Gly Glu Glu Phe Gly Pro Ala
        35                  40                  45

Arg Val His Val Pro Phe Ser Leu Ser His Leu Lys Gln Ile Lys Ile
    50                  55                  60

Asp Leu Gly Lys Phe Ser Asp Ser Pro Asp Gly Tyr Ile Asp Val Leu
65                  70                  75                  80

Gln Gly Leu Gly Gln Ser Phe Asp Leu Thr Trp Arg Asp Ile Ile Leu
                85                  90                  95

Leu Leu Asn Gln Thr Leu Thr Ser Asn Glu Arg Ser Ala Ala Ile Thr
            100                 105                 110

Gly Ala Arg Glu Phe Gly Asn Leu Trp Tyr Leu Ser Gln Val Asn Asp
        115                 120                 125

Arg Met Thr Thr Glu Glu Arg Glu Arg Phe Pro Thr Gly Gln Gln Ala
    130                 135                 140

Val Pro Ser Val Ala Pro His Trp Asp Thr Glu Ser His Gly Asp
145                 150                 155                 160

Trp Cys Arg Arg His Leu
                165
```

<210> SEQ ID NO 32
<211> LENGTH: 286
<212> TYPE: DNA
<213> ORGANISM: MSRV

<400> SEQUENCE: 32

```
cacaggggaa aggaagaaaa tcctactgcc tttctggaga gactaaggga ggcattgagg     60
aagcatacca ggcaagtgga cattggaggc tctggaaaag ggaaagttg ggaaaagtat    120 atgtctaata gggcttgctt ccagtgtggt ctacaaggac actttaaaaa agattgtcca    180
atagaaataa gccaccacct cgtccatgcc ccttatgtca agggaatcac tggaaggccc    240
actgccccag gggatgaagg tcctctgagt cagaagccac taacca                   286
```

<210> SEQ ID NO 33
<211> LENGTH: 95
<212> TYPE: PRT
<213> ORGANISM: MSRV

<400> SEQUENCE: 33

```
His Arg Gly Lys Glu Glu Asn Pro Thr Ala Phe Leu Glu Arg Leu Arg
 1               5                  10                  15

Glu Ala Leu Arg Lys His Thr Arg Gln Val Asp Ile Gly Gly Ser Gly
```

-continued

```
                    20                  25                  30
Lys Gly Lys Ser Trp Glu Lys Tyr Met Ser Asn Arg Ala Cys Phe Gln
            35                  40                  45

Cys Gly Leu Gln Gly His Phe Lys Lys Asp Cys Pro Ile Glu Ile Ser
        50                  55                  60

His His Leu Val His Ala Pro Tyr Val Lys Gly Ile Thr Gly Arg Pro
65                  70                  75                  80

Thr Ala Pro Gly Asp Glu Gly Pro Leu Ser Gln Lys Pro Leu Thr
                85                  90                  95
```

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
tgaagagagt caaaagcagc                                        20